(12) United States Patent
Appel et al.

(10) Patent No.: US 10,040,904 B2
(45) Date of Patent: Aug. 7, 2018

(54) PROCESS FOR PRODUCING A THERMOPLASTIC POLYMER CONTAINING SEGMENTS OF A DIAMIDE

(71) Applicant: DSM IP ASSETS B.V., Heerlen (NL)

(72) Inventors: Wilhelmus Petrus Johannes Appel, Echt (NL); Carel Frederik Constantijn Fitié, Echt (NL); Atze Jan Nijenhuis, Echt (NL); Beert Jacobus Keestra, Echt (NL); Josien Krijgsman, Echt (NL); Michel Henri Chrétien Joseph Van Houtem, Echt (NL); Henricus Marie Janssen, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 10 days.

(21) Appl. No.: 14/911,336

(22) PCT Filed: Jul. 10, 2014

(86) PCT No.: PCT/EP2014/064590
§ 371 (c)(1),
(2) Date: Feb. 10, 2016

(87) PCT Pub. No.: WO2015/022119
PCT Pub. Date: Feb. 19, 2015

(65) Prior Publication Data
US 2016/0200869 A1   Jul. 14, 2016

(30) Foreign Application Priority Data

Aug. 16, 2013 (EP) ..................................... 13180715

(51) Int. Cl.
*C08G 69/44* (2006.01)
*C08G 69/28* (2006.01)
*C07C 231/02* (2006.01)
*C08G 69/40* (2006.01)

(52) U.S. Cl.
CPC ............ *C08G 69/28* (2013.01); *C07C 231/02* (2013.01); *C08G 69/40* (2013.01); *C08G 69/44* (2013.01)

(58) Field of Classification Search
CPC .................................. C08G 69/44; C08L 77/12
See application file for complete search history.

(56) References Cited

U.S. PATENT DOCUMENTS 4,105,640 A * 8/1978 Fortuna ............... C08G 63/6856
528/292
4,473,688 A * 9/1984 Zappa ..................... C08L 77/00
525/432
4,614,815 A * 9/1986 Cognigni .............. C07C 231/02
528/292

(Continued)

FOREIGN PATENT DOCUMENTS

CN  1196738  10/1998
EP  0 835 896  4/1998

(Continued)

OTHER PUBLICATIONS

International Search Report for PCT/EP2014/064590 dated Oct. 8, 2014, four pages.
Written Opinion of the ISA for PCT/EP2014/064590 dated Oct. 8, 2014, six pages.

(Continued)

*Primary Examiner* — Gregory Listvoyb
(74) *Attorney, Agent, or Firm* — Nixon & Vanderhye P.C.

(57) ABSTRACT

Process for the production of a thermoplastic polymer comprising segments of a diamide, the process comprising: 1) a first step of preparing a reaction mixture comprising a diamine $H_2N—Y—NH_2$ Form. (I), and a diester of a dicarboxylic acid Form. (II) 2) a second step of heating the reaction mixture to a temperature at least 5° C. above the crystallization temperature of the diester and a least 5° C. below the melting temperature of the formed amide (formula III) in the presence of an alkaline or earth alkaline alkoxy catalyst Form. (III) wherein X and Y are the same or different and are an aliphatic group comprising 2-12 carbon atoms or an aromatic group comprising 6-20 carbon atoms, R1 and R2 are the same or different and are an aliphatic group comprising 2-15 carbon atoms and wherein R equals R1 or R2 and are the same or different. 3) optionally a third step of quenching the catalyst of the reaction mixture obtained in the second step by adding an acid to the reaction mixture and 4) a fourth step of adding further components to the reaction mixture obtained in the second step, or if the third step has been applied to the reaction mixture obtained in the third step, and so producing the thermoplastic polymer comprising the segments of the diamide.

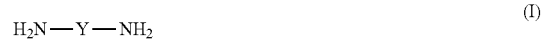
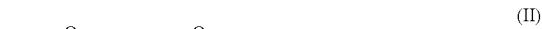
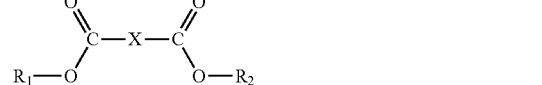

16 Claims, 1 Drawing Sheet

(56) References Cited

U.S. PATENT DOCUMENTS

2010/0093971 A1* 4/2010 Harris .................... C08G 69/44
528/292

FOREIGN PATENT DOCUMENTS

| EP | 0835896 | * | 4/1998 |
|---|---|---|---|
| GB | 1 365 952 | | 9/1974 |
| GB | 2 058 053 | | 4/1981 |
| JP | 53-12987 | | 2/1978 |
| JP | 53-149921 | | 12/1978 |
| JP | 10-273531 | | 10/1998 |
| WO | WO 2008/112833 | | 9/2008 |

OTHER PUBLICATIONS

Niesten et al., "Synthesis and properties of segmented copolymers having aramid units of uniform length", *Polymer*, vol. 41, No. 24, Nov. 1, 2000, pp. 8487-8500.

* cited by examiner

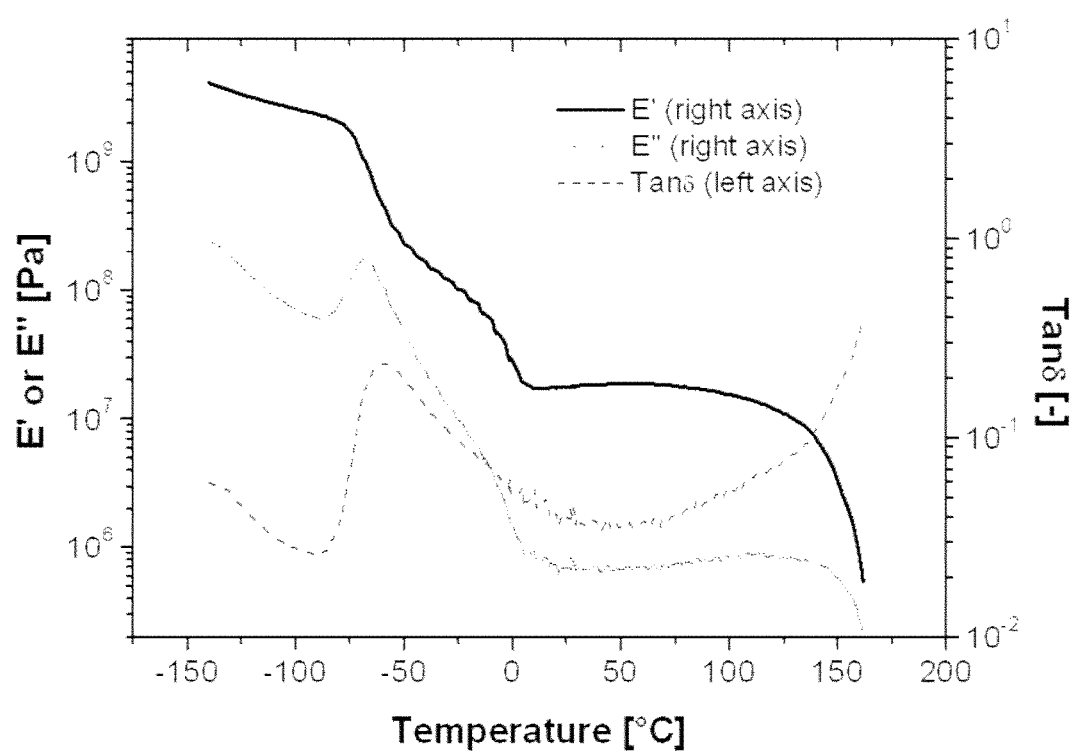

PROCESS FOR PRODUCING A THERMOPLASTIC POLYMER CONTAINING SEGMENTS OF A DIAMIDE

This application is the U.S. national phase of International Application No. PCT/EP2014/064590 filed 10 Jul. 2014 which designated the U.S. and claims priority to EP Patent Application No. 13180715.8 filed 16 Aug. 2013, the entire contents of each of which are hereby incorporated by reference.

The invention relates to a process for producing a thermoplastic polymer containing segments of a diamide, preferably a thermoplastic copolyamide elastomer. A thermoplastic copolyamide elastomer contains hard segments of an amide polymer, oligomer or dimer and soft segments of for example a polyester, a polycarbonate or a polyether. The soft segments have a low glass temperature to provide elastomeric properties at room temperature or even below room temperature. The hard segments crystallize, to form physical cross-links for the thermoplastic elastomer, which melt at elevated temperature.

However there is a distribution in the length of the hard segments, resulting in problems such that the modulus of elasticity is lowered with increasing temperature, also resulting in a lowering of the softening point. Therefore it is important that as much as possible of the hard segments are diamide and that as little as possible tri-amides or even higher amides are present in the hard segments. This also results in fast and full crystallization, even further improving the mechanical properties. This is not only true for thermoplastic copolyamide elastomers, but also for further polymers containing the diamide segments. Furthermore the melt temperature of the diamide is low enough to allow melt polymerization, without the need to use a solvent.

In EP-A-0835896 a process for producing a polyester amide is described, wherein in a first stage a reaction takes place between a diamine and a diester of a dicarboxylic acid in the presence of a catalyst. The so obtained amide is a mixture of amides and to obtain the diamide the amide must be purified by recrystallization, before in a second stage of the process the copolyamide elastomer is produced.

Also in FR 2111288 a process for the production of copolyamide elastomers is disclosed, wherein after the formation of the amide the reaction mixture is purified.

Object of the present invention is a process for the production of thermoplastic polymer, wherein a diamide is obtained with a higher purity, so that the purification step can be omitted.

Surprisingly this object is obtained by providing a process for the production of a thermoplastic polymer comprising segments of a diamide, the process comprising:

1) a first step of preparing a reaction mixture comprising a diamine

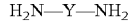

Form. I, and a diester of a dicarboxylic acid

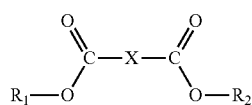

Form. II 2) a second step of heating the reaction mixture to a temperature at least 5° C. above the crystallization temperature of the diester and a least 5° C. below the melting temperature of the formed amide (formula III) in the presence of an alkaline or earth alkaline alkoxy catalyst

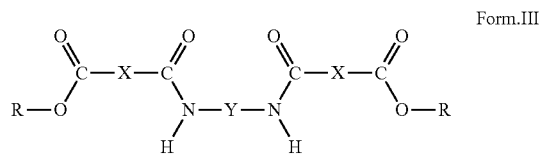

Form.III wherein X and Y are the same or different and are an aliphatic group comprising 2-12 carbon atoms or an aromatic group comprising 6-20 carbon atoms, R1 and R2 are the same or different and are an aliphatic group comprising 2-15 carbon atoms and wherein R equals R1 or R2 and are the same or different.

3) optionally a third step of quenching the catalyst of the reaction mixture obtained in the second step by adding an acid to the reaction mixture and 4) a fourth step of adding further components to the reaction mixture obtained in the second step, or if the third step has been applied to the reaction mixture obtained in the third step, and so producing the thermoplastic polymer comprising the segments of the diamide.

In this way a highly economic process for the production of the polyester amide is obtained.

With the process of the invention a diamide is obtained in the second step that has a higher purity. With purity of the diamide is meant in the context of the present invention the fraction of the diamide in mol % in the compounds containing one or more amine or amide groups.

In the second step the reaction mixture is heated to a temperature at least 5° C. above the crystallization temperature of the diester and a least 5° C. below the melting temperature of the amide. Preferably the reaction mixture is heated to a temperature of at least 10° C., more preferably at least 25° C. above the crystallization temperature of the diester. Preferably the reaction mixture is heated to a temperature of at least 10° C., more preferably at least 25° C. below the melting temperature of the diamide.

The crystallization temperature of the diester and the melting temperature of the amide are measured by DSC, according to ISO 11357-1:1997 under nitrogen atmosphere (purge 50 ml/min) using a heating and cooling rate of 20 K/min.

X and Y are the same or different and are an aliphatic group comprising 2-12 carbon atoms or an aromatic group comprising 6-20 carbon atoms. If X or Y is aliphatic, X or Y may be acyclic or cyclic aliphatic groups. Acyclic aliphatic groups may be linear or branched. Examples of linear aliphatic groups include 1,2-ethylene, 1,3-propylene, 1,4-butylene, 1,5-pentylene, 1,6-hexylene, 1,7-heptylene, 1,8-octylene, 1,9-nonylene, 1,10-decylene, 1,11-undecylene, and 1,12-dodecylene. Preferably 1,4-butylene is used as linear aliphatic group. Examples of branched aliphatic groups include 1,2-propane, 2,3-butane, 1,5-(2-methyl)pentylene, 2,5-hexane, 1,7-(3-methyl)heptylene, 1,9-(5-methyl)nonylene and 2,11-dodecylene. Examples of cyclic aliphatic groups include 1,2-cyclobutylene, 1,3-cyclobutylene, 1,3-cyclopentylene, 1,2-cyclohexylene, 1,3-cyclohexylene, 1,4-cyclohexylene, 2-methyl-1,3-cyclohexylene, 1,3-cycloheptylene, 1,4-cycloheptylene, 1,6-decahydronapthylene, 2,6-decahydronapthylene, 2,7-decahydronapthylene, 1,8- decahydronapthylene, 1,2-cyclohexyldimethylene, 1,3-cyclohexyldimethylene, 1,4-cyclohexyldimethylene and 4,4'-methylenedicyclohexylene. Preferably 1,4-cyclohexylene is used. Examples of aromatic groups include p-phenylene, p-toluylene, p-xylylene, m-phenylene, m-toluylene, m-xylylene, 2,6-toluylene, 2,4-toluylene, 2,6-naphtylene, 2,7-naphtylene, 1,8-napthylene, 1,5-anthracylene, 1,8-anthracylene, 2,6-anthracylene, 2,7-anthracylene, 2,5-furylene, 3,4-furylene, 2,7-fluorenyl, 4,4'-(1,1'-biphenyl)ene, 3,3'-(1,1'-biphenyl)ene, 3,4'-(1,1'-biphenyl)ene, 2,4'-methylenediphenylene and 4,4'-methylenediphenylene. Preferably p-phenylene is used.

R1 and R2 are the same or different and are an acyclic or cyclic aliphatic group comprising 2-15 carbon atoms, preferably 2-12 carbon atoms. If R1 or R2 are an acyclic group the group may be linear or branched. Examples of linear groups include. Ethyl, propyl, butyl, pentyl, hexyl, heptyl, octyl, nonyl, decyl, undecyl and dodecyl. Examples of branched groups include isopropyl, (2-methyl)propyl, tert-butyl, 2-butyl, (2-methyl)butyl, (2-ethyl)butyl, (2-ethyl)hexyl, 3-(6-methyl)heptyl, 4-(3-methyl)nonyl, isononyl, 1-heptyloctyl. Examples of cyclic groups include cyclopentyl, cyclohexyl, cyclohexanemethyl, cyclooctyl, Preferably 2-butyl, (2-methyl)butyl, (2-ethyl)butyl or (2-ethyl)hexyl are used Preferably X, Y, R1 and R2 are selected to obtain a melting temperature of the diamide of at most 280° C., more preferably at most 260° C., most preferably at most 240° C. The melting temperature of the diamide increases in general with increasing weight of the groups X and Y if these groups are aromatic and decreases with increasing weight of the groups X, Y, R1, R2 if these groups are aliphatic.

Preferred diamines include di-aminobutane (DAB, indicated with "4" in the diamide) and p-phenylenediamine (indicated with "phi" in the diamide). Preferred diesters of dicarboxylic acid include diesters of terephthalic acid and (2-ethyl)hexanol (DOT, indicated with "T" in the diamide), the diester of 2,6-naphtalenedicarboxylic acid and (2-ethyl)hexanol (indicated with "N" in the diamide) and the diester of terephthalic acid and butanol (DBT). Preferred diamides therefore include T4T, TphiT, N4N and NphiN.

The molar ratio of diester of the dicarboxylic acid:the diamine in the reaction mixture of the first step may be between 3:1 to 8:1, preferably the molar ratio is between 4:1-6:1. In this way a fast and high conversion is obtained, with a high purity of the obtained diamide.

As catalyst in the second step an alkaline or an earth alkaline alkoxide catalyst is used. Preferably a C2-20 alkoxide catalyst is used. Examples of suitable catalysts include sodium ethoxide, potassium ethoxide, lithium ethoxide, sodium (2-ethyl)hexoxide, potassium (2-ethyl)hexoxide or lithium (2-ethyl)hexoxide may be used. Preferably sodium (2-ethyl)hexoxide is used.

The amount of alkoxyde catalyst used may be between 0.05 and 2.00 mol/mol amine (based on amine content of the reaction mixture in the first step) preferably between 0.05 and 0.5 mol/mol amine.

The catalyst may be added at any stage of the process before or while the reaction temperature has been obtained. Preferably the catalyst is added after the reaction mixture has been molten.

The reaction time is preferably chosen such that the conversion after the second step is more than 80%, more preferably more than 90%, more preferably more than 95%, even more preferably more than 97%, still even more preferably more than 98%.

The conversion is calculated based on the conversion of amine groups into amide groups, as expressed by ([amide]/([amine]+[amide]))100%. The concentration of amide and amine groups in the final reaction mixture is obtained by $^1$H NMR.

To stop the reaction and to neutralize the catalyst, the catalyst may be quenched with an acid in a third step. As acids organic acids, and inorganic acids, and trialkyl ammonium salts or mixtures thereof may be used. Specific examples of acids that may be used include bis(triethylammonium) sulphate, triethylammonium hydrogensulphate, sulphuric acid, hydrochloric acid, triethylammonium chloride and cyanuric acid. Preferably cyanuric acid is used. The amount of acid used may vary between 1.5-0.7 equivalent acid/equivalent alkoxyde catalyst. Preferably the amount is stoichiometric.

After the quenching of the catalyst the reaction mixture is used as such for the polymerization of a thermoplastic polymer in the fourth step of the process according to the invention, without first carrying out a purification step of the diamide.

In the fourth step further components are added to the reaction mixture obtained in the third step and so the thermoplastic polymer comprising the amide segments is produced. Preferably as further component a polymeric diol is added, eventually in the presence of a trans esterification catalyst, for example titanium (IV) n-butoxide, dibutyl tin diacetate.

Preferably the thermoplastic polymer formed in the process according to the invention is a thermoplastic copolyamide elastomer that contains as hard segments the diamide as described above and soft segments for example derived from a polyether, a polyester a polycarbonate or a polyalkane. It is also possible that the soft segments are derived from a dimer fatty acid and/or a derivative thereof. The soft segments may have a glass-transition temperature ($T_g$) of below 0° C. Preferably the $T_g$ is below −20° C., more preferably below −40° C., and most preferably below −50° C.

Preferably the soft segments are derived from a polyether. Suitable aliphatic polyether soft segments are flexible polyethers that are substantially amorphous. The molar mass of the segments may vary within a wide range, but preferably the molar mass is chosen between 400 and 6000, more preferably between 500 and 4000, and most preferably between 750 and 3000 g/mol. Suitable aliphatic polyethers include a poly(alkylene oxide)diol derived from an alkylene oxide of 2-6 C-atoms, preferably 2-4 C-atoms, or combinations thereof. Examples include poly(ethylene oxide)diol, poly(tetramethylene oxide)diol or poly(tetrahydrofuran) diol, poly(neopentylene oxide-co-tetramethylene oxide)diol and poly(propylene oxide)diol. In one preferred embodiment the thermoplastic copolyamide elastomer contains as polyether segments ethylene oxide-terminated poly(propylene oxide)diol segments.

Preferably the reaction mixture contains less than 10 wt. % of solvent in each reaction step, more preferably less than 5 wt. %, even more preferably less than 2 wt. %. In this way an even more economic process is obtained, while running a process with such low amounts of solvent is very well possible with the process according to the invention.

The invention is further explained in the examples.

Methods

Melting Temperature and Crystallization Temperature

The crystallization temperature of the diester and the melting temperature of the amide are measured by DSC, according to ISO 11357-1:1997 under nitrogen atmosphere (purge 50 ml/min) using a heating and cooling rate of 20 K/min.

Relative Viscosity

The relative viscosity was measured at 25° C. in m-cresol at a concentration of 0.1 g/g according to ISO 307 en ISO 1628-5 standards.

Determination of Amine Conversion

The amine conversion was performed by $^1$H-NMR spectroscopy. The peak area of the signal originating from protons attached to the carbon(s) nearest to the amine is compared with the peak area of the signal originating from protons attached to the carbon(s) nearest to the amide.

Determination of Conversion of T4T Synthesis from $^1$H-NMR Spectra

The $^1$H-NMR spectra of the reaction mixture of the diester of terephthalic acid and (2-ethyl)hexanol (DOT or T) and di-aminobutane (DAB or 4) were collected at room temperature on a Varian Mercury NMR spectrometer (400 MHz for $^1$H NMR) in pure deuterated trifluoro acetic acid (TFA-d). The singlet related to the Ar—CH$_3$ signal of toluene was used as internal reference and set to 2.23 PPM. The triplet a originating from the N—CH$_2$ signal of the amide, found at 3.59 ppm, and broad triplet b originating from the CH$_2$—N signal of the amine, found at 3.28 ppm are integrated and the conversion is calculate according to the following formula:

Conversion=int $a$/(int $a$+int $b$)*100%

Determination of Conversion of TphiT Synthesis from $^1$H-NMR Spectra

The $^1$H-NMR spectra of the reaction mixture of the diester of terephthalic acid and (2-ethyl)hexanol (DOT or T) and p-phenylenediamine (phi) were collected at room temperature on a Varian Mercury NMR spectrometer (400 MHz for $^1$H NMR) in a mixture of CDCl$_3$:TFA-D v:v~4:1. The singlet related to TMS was used as internal reference and set to 0 PPM. The singlet a originating from the N—C=CH signal of the amide, found at 7.66 ppm, singlet b originating from the CH=C—N signal of the diamine, found at 7.59 ppm, the doublet c originating from the CH=C—N signal of the monoamide monoamine intermediate, found at 7.49 ppm and the doublet d originating from the CH=C—C—N signal of the ester end groups of the hard block and intermediate, found at 7.98 ppm are integrated and the conversion is calculated according to the following formula:

Conversion=(int $d$)/(int $a$+int $b$+2*int $c$)*100%

Preparation of Test Samples by Compression Molding

Compression molding was used to produce thin film samples for tensile testing and DMTA measurements. The polymer (around 1.5 g) was introduced in a double steal mold (0.200 mm thickness, two 10×10 cm sheets) between two sheets of aluminum foil coated with a releasing agent (Freecoat) and introduced in a press at 180° C. Vacuum was applied and the sample was allowed to melt for 5 min. The sample was then compressed at 30 kN for 3 min. Subsequently the sample was allowed to cool under 180 kN in the water cooled press. When the temperature reached 37° C. the vacuum was removed and the press was opened to yield the compression molded sheets.

Tensile Tests

Tensile tests were performed on ISO-527 5a tensile bars that were punched out from the compression molded films (see above). The dimensions of the samples are measured with a calibrated Heidenhain thickness meter (thickness) and an optical microscope (width). The tests were performed using the following test set-up:
  Machine: Zwick 1455
  Control & analysis: Zwick software, TestXpert II
  Load-cell: 200N cell
  Displacement: Zwick optical extensometer
  Grips fixture: 1 kN pneumatic grips
  Pre-load: 0.2N
  E-modulus speed: 1 mm/min
  Modulus determination: between 0.3 and 0.8% strain
  Test speed: 200 mm/min
  Test conditions: 23° C. & 50% R.H.

The test specimen was extended along its major axis. The modulus was determined at a speed of 1 mm/min, subsequently the tensile test was performed at 200 mm/min until break. A 200N load cell was used for the load measurement. The elongation was determined with an optical extensometer using two reflecting and self-adhesive gauge marks attached to the test specimens. The initial distance between these marks (gauge length) was determined after reaching the pre-load before each test.

DMTA

The dynamic mechanical analyses were carried out in accordance with ASTM D5026 using a TA RSA-III test system at a frequency of 1 Hz and over a temperature range of −130° C. up to 200° C. with a heating rate of 5° C./min. During the measurements the storage modulus (E'), the lost modulus (E") and the tangent delta (tanδ) were determined as a function of temperature. Deviations from the ASTM D5026 were:
  Allowed temperature deviation±2° C. (in standard±1° C.)
  Allowed force deviation±2% (in norm standard±1%)
  Allowed frequency deviation±2% (in standard±1%)
  Heating rate 5° C./min. (in standard 1 to 2° C./min.)

Preparation of Sodium Ethylhexoxide (Alkoxyde Catalyst)

In a dry 100 mL Schlenk flask, sodium metal (pieces stored under mineral oil, 1.45 g) was washed with pentane (3×30 mL) and subsequently dried under argon yielding pure sodium metal (1.22 g, 53.1 mmol). 2-Ethyl hexanol (60.5 mL, 387 mmol) was added and the resulting bubbling suspension was stirred at 40° C. under argon for 26 h, after which still a sodium metal piece was visible. Further stirring at 50° C. for 3 h and at room temperature for 17 h yielded a clear colorless solution which was stored under argon and was used as such. Alkoxide concentration: 1 Molar.

EXAMPLES

Example I

One-Pot Procedure of T4T Synthesis and Polymerization with pTHF 650/250 Soft Block 71.27 grams of the diester of terephthalic acid and (2-ethyl)hexanol and 2.41 grams of N,N'-di-aminobutane were loaded in a glass reactor equipped with a helical stirrer with torque measurement, thermal sensor, distillation tube with vacuum connection and a nitrogen inlet. The reactor was evacuated to 100 mbar and purged with nitrogen three times while stirring to remove any oxygen present. 1.94 grams of a 21 wt. % solution of sodium ethoxide in ethanol was added via a syringe while keeping the reaction medium under a nitrogen atmosphere. The reactor was closed and the mixture was stirred at room temperature overnight (16 hours) under a nitrogen atmosphere. Solid triethylammonium chloride (0.88 grams) was added and the reaction mixture was stirred for an additional 80 minutes. The amine conversion was 95% according to $^1$H-NMR.

Subsequently, the reactor was loaded with pTHF 650 (55.65 grams) (pTHF 650 means pTHF having a number average molecular weight (Mn) of 650 kg/kmol), pTHF 250 (21.50 grams) (pTHF 250 means pTHF having a number average molecular weight (Mn) of 250 kg/kmol), Irganox 1330 (0.25 grams) Ti (80 ppm) and Mg (80 ppm) and the reaction mixture was evacuated to 25 mbar and purged with nitrogen three times while stirring to remove any oxygen present. The reactor was heated to 240° C. and ethylhexanol started to distil. Subsequently the pressure was lowered gradually to a final value of 0.2 mbar to remove condensation products and to increase the molecular weight of the material. The stirring speed was lowered when the viscosity of the melt increased. When a significant melt-viscosity was reached (e.g. significant torque level at low stirring speed), the polymer was unloaded from the reactor and quenched in water.

Example II

One-Pot Procedure of T4T Synthesis and Polymerization with pTHF 2000 Soft Block 22.97 grams of the diester of terephthalic acid and (2-ethyl)hexanol and 1.20 grams of N,N'-di-aminobutane were loaded in a glass reactor equipped with a helical stirrer with torque measurement, thermal sensor, distillation tube with vacuum connection and a nitrogen inlet. The reactor was evacuated to 100 mbar and purged with nitrogen three times while stirring to remove any oxygen present. 0.86 grams of a 21 wt. % solution of sodium ethoxide in ethanol was added via a syringe while keeping the reaction medium under a nitrogen atmosphere. The reactor was closed and the mixture was stirred at room temperature overnight (16 hours) under a nitrogen atmosphere. Solid triethylammonium chloride (0.43 grams) was added and the reaction mixture was stirred for an additional 80 minutes.

Subsequently, the reactor was loaded with pTHF 2000 (91.22 grams), Irganox 1330 (0.26 grams) Ti (80 ppm) and Mg (80 ppm) and the reaction mixture was evacuated to 25 mbar and purged with nitrogen three times while stirring to remove any oxygen present. The reactor was heated to 240° C. and ethylhexanol started to distil. Subsequently the pressure was lowered gradually to a final value of 0.2 mbar to remove condensation products and to increase the molecular weight of the material. The stirring speed was lowered when the viscosity of the melt increased. When a significant melt-viscosity was reached (e.g. significant torque level at low stirring speed), the polymer was unloaded from the reactor and quenched in water. The amine conversion was 94% according to $^1$H-NMR.

Example III

One-Pot Procedure of TphiT Synthesis and Polymerization with pTHF 2000 Soft Block 2268 grams of the diester of terephthalic acid and (2-ethyl)hexanol and 140.1 grams of p-phenylenediamine were loaded in a glass reactor equipped with a nitrogen inlet and stirrer.

180.3 grams of a 1 M solution of sodium 2-ethylhexoxide in 2-ethylhexanol was added via a syringe while keeping the reaction medium under a nitrogen atmosphere. The reactor was closed, the mixture was heated to 100° C. and stirred at 100° C. overnight (20 hours) under a nitrogen atmosphere. The reaction mixture was cooled to approximately 50° C. and solid cyanuric acid (26.66 grams) was added. The reaction mixture was stirred for an additional 60 minutes.

Subsequently, 26.07 grams of the TphiT slurry was loaded in a glass reactor equipped with a helical stirrer with torque measurement, thermal sensor, distillation tube with vacuum connection and a nitrogen inlet. The reactor was loaded with pTHF 2000 (91.19 grams), Irganox 1330 (0.25 grams) Ti (80 ppm) and Mg (80 ppm) and the reaction mixture was evacuated to 25 mbar and purged with nitrogen three times while stirring to remove any oxygen present. The reactor was heated to 240° C. and ethylhexanol started to distil. Subsequently the pressure was lowered gradually to a final value of 1 mbar to remove condensation products and to increase the molecular weight of the material. The stirring speed was lowered when the viscosity of the melt increased. When a significant melt-viscosity was reached (e.g. significant torque level at low stirring speed), the polymer was unloaded from the reactor and quenched in water. The amine conversion was 96% according to $^1$H-NMR.

Example IV

One-Pot Procedure of TphiT Synthesis and Polymerization with pTHF 1000 Soft Block 482.2 grams of the TphiT slurry synthesized in example 3 was loaded in a glass reactor equipped with a helical stirrer with torque measurement, thermal sensor, distillation tube with vacuum connection and a nitrogen inlet. The reactor was loaded with pTHF 1000 (842.7 grams), Irganox 1330 (2.50 grams) Ti (80 ppm) and Mg (80 ppm) and the reaction mixture was evacuated to 25 mbar and purged with nitrogen three times while stirring to remove any oxygen present. The reactor was heated to 240° C. and ethylhexanol started to distil. Subsequently the pressure was lowered gradually to a final value of 1 mbar to remove condensation products and to increase the molecular weight of the material. The stirring speed was lowered when the viscosity of the melt increased. When a significant melt-viscosity was reached (e.g. significant torque level at low stirring speed), the polymer was unloaded from the reactor and quenched in water. The amine conversion was 95% according to $^1$H-NMR.

Example V

One-Pot Procedure of T4T' Synthesis and Polymerization with pTHF 2000 Soft Block (DBT Based)

16.37 grams of the diester of terephthalic acid and 1-butanol (DBT) and 1.21 grams of N,N'-di-aminobutane were loaded in a glass reactor equipped with a helical stirrer with torque measurement, thermal sensor, distillation tube with vacuum connection and a nitrogen inlet. The reactor was evacuated to 100 mbar and purged with nitrogen three times while stirring to remove any oxygen present. 0.89 grams of a 21 wt. % solution of sodium ethoxide in ethanol was added via a syringe while keeping the reaction medium under a nitrogen atmosphere. The reactor was closed and the mixture was stirred at room temperature overnight (18 hours) under a nitrogen atmosphere. Solid cyanuric acid (0.367 grams) was added. The reaction mixture was stirred for an additional 60 minutes.

Subsequently, pTHF 2000 (91.20 grams), Irganox 1330 (0.25 grams) Ti (80 ppm) and Mg (80 ppm) were added and the reaction mixture was evacuated to 25 mbar and purged with nitrogen three times while stirring to remove any oxygen present. The reactor was heated to 240° C. and butanol started to distil. Subsequently the pressure was lowered gradually to a final value of 0.2 mbar to remove condensation products and to increase the molecular weight of the material. The stirring speed was lowered when the viscosity of the melt increased. When a significant melt-viscosity was reached (e.g. significant torque level at low stirring speed), the polymer was unloaded from the reactor and quenched in water. The amine conversion was 95% according to $^1$H-NMR.

Comparative Experiment A.

Comparative experiment A was performed using a purified TphiT hard block as described in Niesten, M. C. E. J., Feijen, J., Gaymans, R. J., Polymer, 2000, 41, 8487-8500. The amine conversion was 95% according to $^1$H-NMR.

TABLE 1

Results of the characterization for polymer synthesized from pure hard block and polymers synthesized In examples I-V and comparative experiment A.

| CE/Ex | Hard block | | | Soft block | $\eta_{rel}$ [—] | DMTA | | Tensile tests | |
|---|---|---|---|---|---|---|---|---|---|
| | Diamide | content [wt. %] | ester/amine [—] | | | $T_g$ [a] [° C.] | E' [b] [MPa] | $\varepsilon_{break}$ [%] | $\sigma_{max}$ [MPa] |
| A | TphiT | 5 | NA | pTHF 2000 DOT based | 3.73 | −72 | 9 | 871 | 17 |
| I | T4T | 5 | 4.3 | pTHF 2000 | 4.40 | −73 | 6 | 1083 | 31 |
| II | T4T | 10 | 6.7 | pTHF 650/250 | 2.92 | −60 | 25 | 1192 | 8 |
| III | TphiT | 5 | 4.5 | pTHF 2000 | 4.57 | −74 | 8 | 1067 | 34 |
| IV | TphiT | 9 | 4.5 | pTHF 1000 DBT based | 3.68 | −69 | 17 | 1481 | 12 |
| V | T4T' | 5 | 4.3 | pTHF 2000 | 4.28 | −73 | 8 | 1053 | 23 |

[a] The glass transition temperature ($T_g$) is determined from the maximum in E".
[b] The storage modulus (E') is reported at 23° C.

The crystallization temperature of DOT is <−70° C.
The crystallization temperature of DBT is −15.8° C.
The melting temperature of TphiT is 232.5° C. (DOT based, (2-ethyl)hexyl ester))
The melting temperature of T4T is 129.8° C. (DOT based, (2-ethyl)hexyl ester))
The melting temperature of T4T' is 203.1° C. (DBT based, (butyl ester))

In FIG. I the DMTA data for the polymer of example IV (E', left axis; Tan δ, right axis) are given.

Discussion On Examples.

Table I shows an overview of the characterization results obtained for polymers synthesized from pure hard block and polymers synthesized according to the invention. The results indicate that all materials synthesized were of sufficient molecular weight to show the desirable mechanical properties associated with TPEs, such as low $T_g$ and high elongation at break. The examples demonstrate that a variety of different soft blocks can be used in the present invention to obtain TPEs with good mechanical properties. Most importantly, the polymers synthesized from pure hard block and the corresponding polymers synthesized according to the invention display highly comparable mechanical properties (CE vs Example III and IV). Furthermore, the DTMA data for the polymer of example IV (FIG. I) proves that the production method disclosed here can yield TPEs with a nearly temperature independent modulus over a large temperature range (0° C.-100° C.) as a results of the high purity of the hard blocks.

In general, these results show that the method disclosed in the present invention presents a facile and industrially feasible production method for TPEs with good mechanical properties that are virtually indistinguishable from the corresponding polymers based on purified hard blocks.

The invention claimed is:

1. A process for producing a thermoplastic polymer comprising amide segments of a diamide, the process comprising:

1) a first step of preparing a reaction mixture comprising a diamine of formula I:

(formula I), and
a diester of a dicarboxylic acid of formula II:

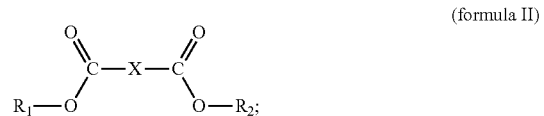

(formula II)

2) a second step of heating the reaction mixture to a temperature at least 5° C. above the crystallization temperature of the diester, as measured by DSC, according to ISO 11357-1:1997 under nitrogen atmosphere with a purge of 50ml/min using a heating and cooling rate of 20 K/min and a least 5° C. below the melting temperature of the formed amid according to formula III as measured by DSC, according to ISO 11357-1:1997 under nitrogen atmosphere with a purge of 50 ml/min using a heating and cooling rate of 20 K/min in the presence of an alkaline or earth alkaline alkoxy catalyst:

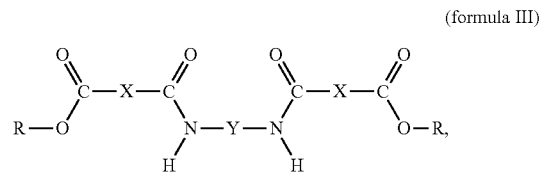

(formula III)

wherein each of X and Y, which may be the same or different, is an aliphatic group comprising 2-12 carbon atoms or an aromatic group comprising 6-20 carbon atoms, each of $R_1$ and $R_2$, which may be the same or different, is an aliphatic group comprising 2-15 carbon atoms, and wherein each R, which may be the same or different, equals $R_1$ or $R_2$;

3) optionally a third step of quenching the catalyst of the reaction mixture obtained in the second step by adding an acid to the reaction mixture; and 4) a fourth step of adding further components to the reaction mixture obtained in the second step, or if practiced to the reaction mixture obtained in the third step, to thereby produce the thermoplastic polymer comprising the amide segments of the diamide, wherein the fourth step comprises a reaction time sufficient to achieve a conversion in the absence of purification of more than 85% of the amine groups to the amide groups as determined by ([amide]/([amine]+[amide]))*100% with concentrations of the amine groups and the amide groups in the reaction mixture being obtained by $^1$H NMR.

2. The process according to claim 1, wherein the temperature in the second step is at least 25° C. below the melting temperature of the formed amide.

3. The process according to claim 1, wherein the temperature in the second step is at least 25° C. above the crystallization temperature of the diester.

4. The process according to claim 1, wherein each of $R_1$ and $R_2$, which may be the same or different, is an aliphatic group comprising 4-12 carbon atoms.

5. The process according to claim 1, wherein the diester of the dicarboxylic acid and the diamine are present in the reaction mixture of the first step to provide a molar ratio of the diester of the dicarboxylic acid: the diamine in the reaction mixture of the first step which is between 3:1 to 8:1.

6. The process according to claim 5, wherein the molar ratio of the diester of the dicarboxylic acid: the diamine in the reaction mixture of the first step is between 4:1-6:1.

7. The process according to claim 1, wherein the reaction time of the fourth step is such that conversion in the absence of purification of the amine groups to the amide groups is at least 90%.

8. The process according to claim 1, wherein the reaction time of the fourth step is such that the conversion in the absence of purification of the amine groups to the amide groups is at least 95%.

9. The process according to claim 1, wherein the acid for quenching is selected from the group consisting of organic acids, inorganic acids, and trialkyl ammonium salts or mixtures thereof.

10. The process according to claim 1, wherein the acid for quenching is an organic acid or a trialkylammonium salt thereof.

11. The process according to claim 1, wherein the acid for quenching is a cyanuric acid.

12. The process according to claim 1, wherein the fourth step comprises adding a polymeric diol as a further component to the reaction mixture.

13. The process according to claim 1, wherein the thermoplastic polymer is a thermoplastic copolyamide elastomer that contains the diamide as hard segments and soft segments derived from a polyether, a polyester, a polycarbonate, a polyalkane, a dimer fatty acid and/or a derivative thereof.

14. The process according to claim 1, wherein the reaction mixture contains less than 10 wt. % of solvent in each reaction step.

15. The process according to claim 1, wherein the reaction mixture contains less than 5 wt. % of solvent in each reaction step.

16. The process according to claim 1, wherein the reaction mixture contains less than 2 wt. % of solvent in each reaction step.

* * * * *